United States Patent
Osypenko

(10) Patent No.: US 11,299,438 B2
(45) Date of Patent: Apr. 12, 2022

(54) METHOD OF OBTAINING A LIQUID ORGANIC BIOFERTILIZER FOR SOIL AND/OR PLANTS, THE BIOFERTILIZER AND METHODS OF USING THE SAME

(71) Applicant: Serhii Osypenko, Kherson (UA)

(72) Inventor: Serhii Osypenko, Kherson (UA)

(*) Notice: Subject to any disclaimer, the term of this patent is extended or adjusted under 35 U.S.C. 154(b) by 109 days.

(21) Appl. No.: 16/755,883

(22) PCT Filed: Oct. 17, 2018

(86) PCT No.: PCT/UA2018/000114
§ 371 (c)(1),
(2) Date: Apr. 14, 2020

(87) PCT Pub. No.: WO2019/078806
PCT Pub. Date: Apr. 25, 2019

(65) Prior Publication Data
US 2020/0299205 A1    Sep. 24, 2020

(30) Foreign Application Priority Data

Oct. 17, 2017  (UA) .............................. a 2017 10006

(51) Int. Cl.
| | | |
|---|---|---|
| C05F 11/00 | (2006.01) | |
| C05F 11/02 | (2006.01) | |
| C05F 11/08 | (2006.01) | |
| C05G 5/27 | (2020.01) | |
| C05F 17/20 | (2020.01) | |

(52) U.S. Cl.
CPC .............. *C05F 11/00* (2013.01); *C05F 11/02* (2013.01); *C05F 11/08* (2013.01); *C05F 17/20* (2020.01); *C05G 5/27* (2020.02)

(58) Field of Classification Search
None
See application file for complete search history.

(56) References Cited

U.S. PATENT DOCUMENTS

| | | | | |
|---|---|---|---|---|
| 6,471,741 | B1* | 10/2002 | Reinbergen .............. | C05G 5/23 71/6 |
| 2004/0261481 | A1* | 12/2004 | Anaya-Olvera ........ | C05F 11/02 71/24 |
| 2006/0058566 | A1* | 3/2006 | Shulgin ..................... | C02F 1/54 588/316 |
| 2018/0057419 | A1* | 3/2018 | Rezai ........................ | C05B 7/00 |

* cited by examiner

*Primary Examiner* — Wayne A Langel
(74) *Attorney, Agent, or Firm* — Inventa Capital PLC

(57) ABSTRACT

The invention relates to the production and use of environmentally friendly liquid organic biofertilizer for soils and/or plants which is colonized by natural soil microorganisms. It is proposed the method in which, due to the optimal processing of a starting humus-containing soil or soil mixture colonized by natural soil microorganisms with applying the proposed "soft" controlled turbulence action without cavitation effects, the conditions for preserving and reproducing the natural soil microorganisms in their natural medium are provided, as a result it is obtained the final product in the form of a homogenous fine-dispersed suspension, which contains the solids of 10-50 microns size. This product is mainly composed of water-soluble nitrogen (preferably 40 mg/100 g fertilizer) and water-soluble carbon (preferably 470 mg/100 g fertilizer) and is suitable for packaging and long-term storage. The claimed biofertilizer is uniformly colonized by the hardened natural soil microorganisms which are in the state of anabiosis and spore forms, their concentration being at its maximum. The proposed treating soil, seeds or plants with using this biofertilizer results in higher crop yields, improved fertility of depleted soils and restored fertility of sandy and sandy-loam soils.

15 Claims, No Drawings

METHOD OF OBTAINING A LIQUID ORGANIC BIOFERTILIZER FOR SOIL AND/OR PLANTS, THE BIOFERTILIZER AND METHODS OF USING THE SAME

TECHNICAL FIELD

The present invention relates to agriculture and, more specifically, to the production and use of the environmentally friendly organic biofertilizer, namely, to the liquid organic biofertilizer for soils and/or plants colonized by natural soil microorganisms. The invention can be most widely used in restoring the fertility of soils depleted of nutrients and natural microorganisms as a result of the intensive use of chemical fertilizers and pesticides, under flooding, etc, as well as in improving seed germinating capacity and increasing plant yield, especially in case of drought and late frosts.

BACKGROUND ART

Presently it has been proved (at postulates level) that plants cannot exist without symbiosis and association with microorganisms. Plant roots and microorganisms create a peculiar "cover"—the rhizosphere which provides necessary conditions for plants proper nutrition and their protection against pathogens. Therefore it is just the complexes of beneficial microorganisms within the soil—plant—microorganism system that help to optimally realize soil and plant potential capabilities and get quality yields. It is this reason that stimulated microbiological approaches to increasing soil fertility and ensuring higher productivity of the agrarian sector in different countries of the world.

The basis of these approaches is the selection of soil microorganism beneficial strains and the creation of optimal conditions for their reproduction on artificial nutrient media to obtain high concentrations of $10^9$-$10^{10}$ microorganisms per 1 g of medium. The microorganisms which are considered "beneficial" are firstly nitrogen-fixing microorganisms, such as *Rhizobium, Bradirhizobium, Azotobacter*, phosphorous-mobilizing mostly from the *Bacillus Subtilis* species, *lactobacillus*, etc. At the same time, scientists—practitioners agree that the effectiveness of artificially created biological products does not exceed 65-70%, especially in extreme natural conditions, such as drought, high and low temperatures, soil underflooding. Bacteria which have been artificially created on culture media rich in organic matter cannot quickly be adapted to depleted soils and contaminated by chemicals and soon die reducing its initial concentration thousands of times. For example, bacteria grown artificially on BEA (beef-extract agar) with a level of ammonium nitrogen equals 120-130 mg/100 g, are decreased in number from the initial titer of $5·10^9$ to $2·10^6$ pera gram within only 1-2 days after getting into peat mixture with natural nitrogen level of 30-40 mg.

A known method for obtaining highly concentrated nitrogen-fixing bacterial preparations includes mixing a conventionally grown bacterial suspension with peat and adding into this mixture an aqueous extraction of biohumus as a source of biologically active compounds for limiting the development of fungal microflora (UA, 47304 A). In the preferred best embodiment of this method non-sterile peat is used and dextrin (about 2%) is added to the mixture to increase the growing capacity.

The time of preparing the final product is more than 20 days not considering the time of preparing a bacterial culture in liquid nutrient medium. Dependence on the poorly controlled quality of the biohumus does not guarantee the stability of the final product in addition the long preparation time is a disadvantage of this known method.

It is known also the alternative methods of obtaining biological compounds for increasing yields and controlling plant pathogens, which are more environmentally friendly and harmless to animals and humans and which contain useful natural microorganisms. A typical example of such methods is the method of producing biocompositions based on *Bacillus, Brevibacillus* and/or *Paenibacillus* strains (WO2008/025108 A1). Microorganism compositions, as described in this document, are made up of "wild type" bacteria, which requires an uneasy way of isolating these bacteria strains from the natural medium.

An example of another natural bacterium use (*Pseudomonas fluorescens* plant pathogen destroyer) for combating with plant diseases and increasing yields is disclosed by U.S. Pat. No. 6,495,362.

Although these methods seem to be more biological due to using natural (wild) soil bacteria, it should be noted that the technology of isolating necessary strains from the natural environment is rather complicated, besides, these bacteria are quite selective for destructing only certain species of natural plant pathogens.

Growing these bacteria concentrates on an artificial nutrient media which are different from natural soils complicates the process and prolongs the time of adapting "foreigners" to a new place and creating the necessary "soil-plant-microorganism" biological complexes.

Manufacturers of such concentrates do not take into account the fact that artificial bacteria cannot quickly adapt to the new living conditions thereby increasing significantly the so-called lag phase and reducing the essential efficiency of these biological preparations.

In addition, by isolating one or another strain of a beneficial microorganism, researchers disregard the symbiotic, metabolic and antagonistic interactions between microorganisms living in natural conditions. Thus, the development of anaerobes in well-aerated soils is impossible without aerobes that absorb free oxygen.

For this reason it is advisable not to destroy the microbiota living in sufficient quantity and natural symbiosis in fertile soils, peat bogs, sapropel deposits and the similar natural environment, it is better to create the necessary conditions for its preservation and reproduction. That is why in order to increase yields, especially those of legume crops, at the beginning of the last century agrarians sowed seeds together with particles of soil and roots taken from the fields where legumes had grown in the previous year. The introduction of fertile soil particles with beneficial microflora into new plots is used even now but mainly on household plots. It is clear that such technology is ineffective, since the average microbiota amount on fertile soils rarely exceeds $10^4$-$10^5$ microorganisms/gram and, moreover, the removal of the upper soil layer upsets the current balance in the environment.

There are various methods of reproducing microbiota of the starting material. For example, it is known the method of obtaining a fertilizer from sapropel according to which silt is heated with superheated steam to destroy pathogenic microorganisms, the steam temperature is 200-600° C. to activate soluble carbon and to reproduce the biological decomposition of the silt by using non-pathogenic microorganisms that remain in the silt after heating. The disadvantage of this method is significant environment pollution by steam emissions into the atmosphere, uneven heating of large silt amounts on open grounds and, accordingly, ineffective destruction of the pathogenic microflora to obtain quality fertilizers.

A more environmentally friendly method is the method of processing of waste waters and organic materials of these waters by cavitation using a rotor-stator mixer or a mill and converting the processed material into the "Bio-solids" mulch (US, 20050108930 A1). Unfortunately, these fertilizers cannot be used as organic due to the large number of chemical impurities that are hazardous to the main agricultural plants, therefore they are considered rather as a nutrient medium for decorative city plantations and lawns. In addition, their natural microbiota is far from symbiotically adapted microorganisms of fertile soil.

Also it is known the biological fertilizer which contains nitrogen, phosphorus, potassium, calcium, magnesium, iron, manganese, copper, water-soluble humates and agronomical useful biological flora of the biohumus (RU, 2181710).

The disadvantage of this product is its low level of content of the agronomical useful biological bioflora, which leads to a significant decrease in a fertilizer efficiency. The reason for the low content of bioflora is that during mixing the biohumus and peat mixture in the reactor, a significant number of microorganisms just die when potassium alkali chemical solution is added and during filtering a large number of viable microflora stays in the sediment.

The particles of the active substance solids (biohumus and peat) contained in the final product cause the clogging of the sprayer apertures due to their excessive size. In addition, they can settle on the bottom of the container in which fertilizer is stored. Thus, the physical state of this known fertilizer can be characterized as a suspension of an inorganic origin with low dispersion and stability, its use for spraying plants being problematic.

In these prior art methods rather "tough" means of treating one or another biologically active medium were used to increase the availability of its beneficial components and at the same time to reduce the amount of plant pathogenic microorganisms and fungi.

Such "selectivity" of approaches, that is, the desire to remove "everything harmful" and save and reproduce "everything beneficial" is quite complicated and probably practically impossible task.

This opinion is confirmed by numerous studies of exactly the opposite direction, in particular pasteurization of food liquids by means of cavitation effects [CA, 2 511 744]. Thin coats of bacteria do not bear the cavitation pressure pulsations and are effectively destroyed.

There are a lot of convincing evidences on the bacterial microflora destruction by "tough" cavitation effects on the processed fluid. Reference can be made to the following documents of the prior art:

- ultrasonic cavitation [RU, 2109688 C1, US, 20080257830 A1, U.S. Pat. No. 9,174,189 B2, WO2009/118002A2];
- acoustic cavitation [EP, 1800744 A1, RU, 2396216 C1];
- cavitation effects by rotary-pulsating disperser, including those operating in the resonant acoustic oscillations mode [RU, 2396216 C1, RU, 2305073 C2, RU, 2420500 C1, RU, 2304561 C2];
- flow-type hydrodynamic cavitators such as Pito tube with obstacles having sharp edges and cracks, etc. [RU, 2585635 C1, RU, 2603391 C1, WO2012/005631 A2].

The authors of these publications specify different process parameters as a criterion that causes cavitation bulbs collapse and subsequent bacterial microflora destruction, in particular, the great amount of the specific energy per area unit or volume unit in the active zone of acoustic effect.

In practice, this means that the higher the energy intensity of the process, the more intense destruction of bacteria, especially relatively large ones, is caused by the cavitation process.

UA, 87342 C1 discloses the method of producing a liquid biological fertilizer and the fertilizer itself which are the most relevant to the claimed group of inventions. This known fertilizer contains partly preserved agronomical beneficial biological bioflora but for obtaining this fertilizer biohumus is subjected to dispersion by means of a hydrodynamic cavitation disperser to obtain a finely dispersed water suspension with the biohumus particles of 3-10 microns. Accordingly, after such processing which leads to fine and aggressive crushing of solids of the nutrient medium a significant part of the unique bacterial microflora in the processed humus medium, particularly large-sized bacteria, will be destroyed.

It is disclosed that "smaller particle size leads to increasing surface area on which microorganisms can be immobilized".

The characteristic sizes of beneficial soil bacteria are known to differ considerably. Thus, the characteristic sizes of nitrogen-fixing bacteria of the *Rhizobium* and *Bradirhizobium* type are bigger than the typical sizes of phosphorous-mobilizing bacteria of the *Bacillus* type and are about 3-5 microns.

This means that preservation and selection of the beneficial microbiota of the starting species composition, in particular, of beneficial natural (wild) soil bacteria living in natural humus soils, peatlands, sapropel deposits, etc., is impossible by using this method, since the known technology provides "tough" and aggressive cavitation effect on the processed medium, which changes substantially the starting species composition of the natural soil microorganisms.

UA, 87342 C2 also discloses that "the contact of microorganisms with biohumus fine-dispersed inclusions of biohumus occurs under the influence of airlift flows of air bubbles containing oxygen".

But the cavitation effect on the gases dissolved in flowing liquid media of the solid phase-liquid type under constant access of oxygen is chemically and biologically aggressive. Because of its unpredictability and uncontrollability there are negative effects related to the effective changes in natural microbiota of the species composition (for example, towards aerobic bacteria) and excessive oxidation of natural soil beneficial components, which causes as a result a significant distortion of the final product bacterial profile if compared to the initial bacterial profile at the beginning of the treating process.

SUMMARY OF THE INVENTION

The above mentioned problems lead to the need to create such a method of obtaining a liquid organic fertilizer for soils and/or plants colonized by natural soil microorganisms that could provide optimal conditions for reproducing and preserving substantially the starting species composition of natural soil microorganisms in the final product by using a special and unique technology of "soft" turbulent effect with no cavitation effects. This final product should be in the form of a homogeneous fine dispersion suspension with solids of 10-50 microns, which is bigger than the size of relatively large microorganisms (5-10 microns), be suitable for packing and long-term storage and contain carbon and nitrogen-containing substances in water-soluble forms and the hardened natural soil microorganisms of the starting species composition in the state of anabiosis and spore forms with the highest possible concentration. The optimal methods of using this final product should provide the conditions of obtaining higher crop yields, improved fertility of depleted soils and restored fertility of sandy and sandy-loam soils.

The problems are solved by the proposed method of obtaining liquid organic biofertilizer for soils and/or plants which is colonized by natural soil microorganisms and includes the following operations:

a) preparing, sorting and crushing a portion of a starting humus-containing soil or soil mixture, in which at least one of soils in the mixture is a humus-containing, the starting humus-containing soil having beneficial components which contain an organic carbon in an amount greater than 10% and an organic nitrogen in an amount greater than 1% and having colonies of natural soil microorganisms, their concentration in the starting humus-containing soil or soil mixture being not less than $10^4$ CFU/ml;

b) mixing the crushed portion of the said soil or soil mixture with water to produce a water suspension;

c) creating a running flow of said water suspension within a closed circuit with oxygen-eliminating;

d) cyclic processing of the running flow of the water suspension within the closed circuit with oxygen-eliminating by using a turbulence effect so as to preclude cavitation and due to turbulent friction and shearing force to provide for crushing solids in a processed medium of the running flow of the said water suspension and uniform heating of a whole volume of the processed medium with a temperature growth rate not exceeding 2° C./min; said cyclic processing comprising at least two stages, a first stage and a second stage.

The first stage provides an initial heating of the processed medium, extracting of carbon- and nitrogen-containing substances from the processed medium, transiting these substances into water-soluble forms with simultaneous crushing solids in the processed medium and as a result obtaining a homogeneous processed medium with carbon- and nitrogen-containing substances in water-soluble forms causing a growth of colonies of natural soil microorganisms present in the homogeneous processed medium. When reaching a predetermined final temperature upon the initial heating, which depends on a species composition of the natural soil microorganisms containing in the starting humus-containing soil, it is achieved a growth of substantially all kind of colonies of the natural soil microorganisms present in the starting humus-containing soil to concentrations exceeding $10^8$ CFU/ml and a uniform colonization of the homogeneous processed medium with carbon- and nitrogen-containing substances in water-soluble forms by these microorganisms.

The second stage provides a further heating the homogeneous processed medium and a further crushing solids in the homogeneous processed medium to result in hardening substantially all kinds of the natural soil microorganisms present in the homogeneous processed medium, transiting these microorganisms into an state of anabiosis and spore forms and crushing solids in the homogeneous processed medium to the sizes in the range of 10-50 microns.

The method according to the claimed invention comprises also the final step e) which provides:

removing the homogenous processed medium from said closed circuit after finishing the second stage followed by cooling said medium to result in obtaining a final product in the form of a liquid organic biofertilizer for soils and/or plants. This final product is suitable for packaging and long-term storage and contains carbon- and nitrogen substances in water-soluble forms, solids with size of 10-50 microns and the hardened natural soil microorganisms substantially of all kind present in the species composition of the starting humus-containing soil that are in the state of anabiosis or spore form and in the concentration exceeding $10^7$ CFU/ml.

The method according to the invention completely eliminates the transition of the processable suspension flow into the cavitation with characteristic cavities and pockets, which prevents the destruction of a relatively large microorganisms such as *Rhizobium* or nodule bacteria.

The lower limit of crushing (10 microns) should be greater than the maximum size of the typical fertile soil bacteria, which prevents their destruction, while the upper limit should be 50 microns to meet the requirements of modern sprayer filter construction.

It is also necessary to emphasize that it is very important that the final product is obtained in form of the homogenous fine-dispersion suspension because it is just this form that causes the transition of the beneficial components of the starting humus-containing soil into water-soluble form which is indispensable both for the microflora active growth and for the macro and micro nutrition of germinating seeds and growing plants when using this product as a fertilizer.

According to the next preferred embodiment of the claimed method the optimal heating temperatures for cyclic processing at the first stage may be up to about 50° C., at the second stage—within the range of 50°-80° C., while the optimal cooling temperatures may be from +40° C. to −4° C., cooling to subzero temperatures ensuring additional hardening of microorganisms.

It is advisable to use a starting soil selected from the group consisting of peat, forest soil, sapropel, freshwater estuary and lake deposits, algae, biohumus, black earth, grey earth and leonardite. If the starting humus-containing soil or soil mixture has a lignin content amounting to more than 2% measured on a dry matter basis, the final product will be obtained in a gel-like form which is very usable and if the starting humus-containing soil or soil mixture has a humus content amounting to more than 3% measured on a dry matter basis, the final product will contain more than 0.1% humus water-soluble acids.

In the other preferred embodiment of the claimed method it is expedient to use microorganisms chosen from the group consisting of nitrogen-fixing bacteria, or nitrifiers, such as *Rhizobium*, bacteria that assimilate organic nitrogen from soils such as *Azotobacter*, phosphorous-mobilizing bacteria such as *Bacillus Subtilis*, oligotrophic bacteria that grow well in the depleted soils and fungal microflora including micromycetes. All these natural soil microorganisms upon hardening at the step d) of the proposed method are transiting to an state of anabiosis or spore forms and present in these state and forms in the final product.

In addition one more preferred embodiment of the claimed method includes a possibility to carry out the cyclic processing in a closed circuit with oxygen elimination containing a vertical cylindrical tank, an electric pump connected to the cylindrical tank lower part and a turbulence device with a turbulence nozzle mounted after the pump and tangentially connected to the cylindrical tank upper part. According to this embodiment it is additionally advisable that mode of turbulence effect on the medium processed in this closed circuit may be provided so as to exclude cavitation and emergence of dead zones by keeping the following three conditions:

$$0.1 \text{ Bar} \leq \Delta P \leq 0.2 \text{ Bar} \quad (1)$$

$$0.1 \frac{\text{kW}}{\text{kg}} \leq \overline{N} \leq 0.2 \frac{\text{kW}}{\text{kg}} \quad (2)$$

$$T_1 = T_2 \ldots T_n \quad (3)$$

where $\Delta P = (P_1 - P_2)$—pressure difference before and after the turbulence nozzle (Bar), $\overline{N} = \frac{N}{M}$ - process specific energy consumption, kW/kg, N pump electric drive power, kW, M—processed fluid medium weight, kg, $T_1 = T_2 \ldots T_a$—current heating temperature at measuring points distributed on an outer surface of the cylindrical tank which serve to control the uniformity of heating the entire volume of the medium processed in the closed circuit.

The proposed according to the invention cyclic processing of the water suspension flow in the closed circuit without access to oxygen by turbulence effect in the mode that excludes cavitation may be best realized, for example, using the devices developed by Sergey Osypenko, the author of the present invention, and protected, in particular, by patents CA, 2511744 and UA, 42365.

In such devices the closed circuit is created by joining a vertical cylindrical tank to the pump through a sucker connected either to the tank lower part in its center on the continuation of the symmetry axis—patent CA, 2511744 (in this case the tank has a conical lower part connected to the tank cylindrical surface or to the pump tangential to the tank lower part in the direction of fluid rotation (patent UA, 42365) and tangential through a delivery nozzle to the tank upper part. The turbulence device is fixed on the delivery pipe.

The author has found that the proposed soft turbulence effect on the processed medium and slow heating, the rate not exceeding 2° C./min, which excludes cavitations and dead zones in the closed circuit, may be best implemented by using any one of the above devices provided the above mentioned requirements 1), 2) and 3) are fulfilled during cyclic processing at stage d) according to the claimed method.

Exceeding pressure differential $\Delta P = (P_1 - P_2)$ over 0.2 Bar testifies to cavitation start. In this case lower pressure at the pump outlet $P_1$ which prevents cavitation can be ensured by the pump drive speed control.

$\Delta P$ value drop below 0.1 Bar decreases the turbulizer effect on the medium to be processed, which results in a substandard final product.

$T_1, T_2 \ldots T_n$ sensors serve to control dead zone appearance. The change in their readings by 2-3° C. testifies to the appearance of such a zone near the sensor with a lower temperature. As the temperature grows the medium viscosity grows and the probability of such zones increases.

Thus, the optimal process mode suggested by the claimed method provides controllability and reliability of cyclic processing without cavitation effects and dead zones with a limited heating rate which results in the improvement of the final product quality.

According to the second aspect of the present invention it is claimed a liquid organic biofertilizer for soils and/or plants per se which is obtained by the claimed method. The claimed biofertilizer contains a water-soluble nitrogen and a water-soluble carbon, solids with size in the range of 10-50 microns and a hardened natural soil microorganisms substantially of all kind present in the species composition of the starting humus-containing soil which are in the state of anabiosis of or in spore forms and are uniformly populated in this biofertilizer in the concentrations exceeding $10^7$ CFU/ml.

Preferably a content of the water-soluble nitrogen is at least 40 mg and a content of the water-soluble carbon is not less than 470 mg per 100 g biological fertilizer on basis of a dry weight.

According to the third aspect of the present invention it is claimed a method of treating soil, seeds or plants with using the liquid organic biofertilizer obtained by the claimed method of claims 1-8. This method comprises the following steps: adding a liquid or a crushed dry natural soil to the obtained biofetilizer to reduce the concentration of hardened natural soil microorganisms present in it in the state of anabiosis and spore forms to the concentration exceeding $10^4$ CFU/ml, and applying such biofetilizer of reduced concentration to a soil before sowing or during the sowing period or treating seeds or plants with such biofertilizer during the vegetation period before harvesting. According to the different preferred embodiments of the proposed treating it is now possible to improve a yield of a specific crop, to increase the fertility of the depleted or to restore sandy and sandy-loam soils.

BEST MODE FOR CARRYING OUT THE INVENTION

The claimed invention is further described in more detail with reference to the accompanied Examples which disclose the different preferred embodiments in various aspects of the claimed invention.

In present application the term "natural soil microorganisms" means substantially all native soil microbiota divided into four types: bacteria and fungi as the basis of any soil as well as actinomycetes and yeast as intermediate forms between bacteria and fungi which are specific for each particular type of soil, highly variable depending on changes in external conditions.

Without exaggeration it should be point out the dominant role of the bacteria in soil fertility and plant productivity. Thus, if fungi have greater effect on plants, the bacteria—both on plants and soils, that is, they are directly involved in transformation and circulation of organic matter in the soil—plant—atmosphere—soil chain. Bacteria are more susceptible to chemicals in soil. Fungi populations are less susceptible to anthropogenic impact.

It is for this reason the bacteria have been chosen as the main representatives of fertile soil microorganisms and their main species have been studied. The control over fungal microflora has been carried out only as to its total number, without dividing it into classes and species.

According to the modern concept, the number of major bacteria types has long exceeded a thousand and their classification is very difficult and is the subject of scientific debate and controversy. Therefore, having no opportunity to produce a purely scientific proof of preserving the whole bacterial profile of natural soils, the Examples below will demonstrate data confirming the preservation in the final product obtained by the claimed method substantially the same fertile soil microorganisms present in the species composition of the starting humus-containing soil (the same "microbiotic portrait") (Example 1), and preservation of certain significant bacteria types, which confirms the achievement of unobvious technical results of the claimed method of obtaining the final product in the form of a biofertilizer which provides the minimal disturbing natural balance of the soil microorganisms (Examples 2-11).

Example 12 is presented for comparing the result of the peat suspension processing, the suspension humidity being 80%, the analyses were made before and after the processing. Example 13 is presented in order to demonstrate an increase in fertility and yields when cultivating the Aratta soybean variety under irrigation. In all cases nitrogen-fixating bacteria of the *Rhizobium* and Bradirhizobium type have been selected as bacteria of "large" size (up to 5 microns and above). Even larger sizes have been registered with oligotrophic bacteria which are widespread in depleted soils, peat, sandy-loam soil, etc. In order to adapt to harsh living conditions with a poor nutrition these bacteria have a large contact surface, that is, large size (up to 10 microns) due to the formation of special overgrowths, flagella, etc.

As an example of relatively small bacteria (1-2 microns or lower) numerous species of phosphorous-mobilizing bacteria of the *Bacillus Subtilis* type have been selected. These bacteria are very important in transforming an organic phosphorous which is contained in plant in soil into the mineral form available for growing plants.

Numerous bacteria of the *Azotobacter* type are mainly related to microorganisms that grow well in the presence of oxygen, that is, to aerobic bacteria. At the same time some of them are relative aerobes, while others are anaerobes, for example, *Clostridium Azotobacter*.

It should be noted that due to the presence of a large number of relative aerobes and anaerobes in soil, the artificial aeration of nutritious substrates as well as suspensions from biohumus, vermicompost, etc used in well-known technologies results in a substantial distortion of the natural soil bacterial profile towards the aerobic bacteria.

To obtain a microbiological "portrait" before and after applying the method according to the invention, the following typical microorganisms conventionally tested on appropriate nutrient media have been used:

1. Nitrogen-fixing bacteria or nitrate-fixers, including *Rhisobium*, are tested on Ashby nutritional medium;
2. Bacteria capable of assimilating soil organic nitrogen forms of the *Azotobacter* type are tested on the SAA (starch—ammonia agar) medium;
3. Oligotrophic bacteria which develop well on depleted soils are tested on SA (starvation agar) medium;
4. Phosphorous-mobilizing bacteria of the *Bacillus Subtilis* type are tested on Gause's medium;
5. Fungi microflora including *Trichoderma* and micromycetes are tested on Czapek's medium;
6. The total amount of microorganisms is tested on Zvyagintsev's medium.

Example 1

Research has been carried out using an organic valley peat diluted with water, the ratio being 1:1.25, as starting humus-containing soil. The resulting suspension was obtained according to the claimed method.

During obtaining the medium was studied by microbiological and plant pathological methods. In compliance with the conventional estimation of the soil composition the qualitative and quantitative microbiota composition was tested in the following titres: fungi and micromycetes—$1:10^{-3}$, bacteria—$1:10^{-4}$.

The results obtained are given in tables 1-4.

TABLE 1

Fungi microbiota and micromycetes of liquid soil samples under study ($1:10^{-3}$ titre, wort agar)

| No | Temperature t° (degrees) | Average colonies number | Notes |
|---|---|---|---|
|   | Feedstock before processing, 20° C. | $2.1 \cdot 10^3$ | 4 Aspegillus colonies, 50 mm d |
| 1 | 30° C. | $4 \cdot 10^3$ | -«- |
| 2 | 40° C. | $7.5 \cdot 10^3$ | More Penicillium |
| 3 | 50° C. | $4 \cdot 10^4$ | -«- |
| 4 | 60° C. | $3.1 \cdot 10^6$ | sharp increase in fungi and micromycetes number |
| 5 | 70° C. | $2 \cdot 10^3$ |  |
| 6 | 80° C. | $1.2 \cdot 10^2$ | spore and inactive forms |
| 7 | 90° C. | traces | practically no |

TABLE 2

Nitrogen-fixing mictobiota (*Rhizobium*, *Bradirhizobium*, etc) of liquid soil samples ($1:10^{-4}$ titre, Ashby medium)

| No | Temperature t° (degrees) | Average colonies number (*Azotobacter*) | Notes |
|---|---|---|---|
|   | Feedstock before processing, 20° C. | $3.2 \cdot 10^5$ | mainly *Rhizobium* |
| 1 | 30° C. | $2 \cdot 10^8$ | -«- |
| 2 | 40° C. | $3.5 \cdot 10^7$ | -«- |
| 3 | 50° C. | $2.2 \cdot 10^8$ | mainly *Rhizobium* and *Bradirhizobium* |
| 4 | 60° C. | $1.7 \cdot 10^7$ | -«- |
| 5 | 70° C. | $2.3 \cdot 10^7$ | mainly spore forms |
| 6 | 80° C. | $1.3 \cdot 10^7$ | -«- |

TABLE 3

Total amount of bacterial microbiota of liquid soil samples containing mainly organic nitrogen compounds ($1:10^{-4}$ titre, beef-extract agar)

| No | Temperature t° (degrees) | Average colonies number | Notes |
|---|---|---|---|
|   | Feedstock before processing, 20° C. | $1.4 \cdot 10^4$ | 7 main morphological types, standard forms |

TABLE 3-continued

Total amount of bacterial microbiota of liquid soil samples containing mainly organic nitrogen compounds ($1:10^{-4}$ titre, beef-extract agar)

| № | Temperature t° (degrees) | Average colonies number | Notes |
|---|---|---|---|
| 1 | 30° C. | $2.5 \cdot 10^4$ | -«- |
| 2 | 40° C. | $7.4 \cdot 10^7$ | -«- |
| 3 | 50° C. | $8.2 \cdot 10^8$ | -«- |
| 4 | 60° C. | $3 \cdot 10^8$ | -«- |
| 5 | 70° C. | $4.1 \cdot 10^8$ | 2 bacillary morphological types (10-15 mm d) |
| 6 | 80° C. | $5.6 \cdot 10^7$ | bright yellow ones of the *Sarcina* type, 3 other saprophyte types, white color |
| 7 | 90° C. | $3.5 \cdot 10^5$ | one viable bacterium |

TABLE 4

Total amount of microbiota of liquid soil samples ($1:10^{-4}$ titre, Zvyagintsev's medium)

| № | Temperature t° (degrees) | Average colonies number | Notes |
|---|---|---|---|
|  | Feedstock before processing, 20° C. | $1.8 \cdot 10^5$ | practically all morphological types |
| 1 | 30° C. | $2.3 \cdot 10^5$ | -«- |
| 2 | 40° C. | $7.1 \cdot 10^7$ | -«- |
| 3 | 50° C. | $3.4 \cdot 10^8$ | -«- |
| 4 | 60° C. | up to $3 \cdot 10^{10}$ | widest quality range of all morphological types |
| 5 | 70° C. | $7 \cdot 10^9$ | spore formation |
| 6 | 80° C. | up to $6.7 \cdot 10^7$ | spore and atypical forms |
| 7 | 90° C. | $2.1 \cdot 10^7$ | bacillary + spore forms |

Table 1 shows sharp increase in fungi and micromycetes amounts in the temperature range of 50°-60° C. up to $3.1 \cdot 10^8$ compared to the control ($2.1 \cdot 10^3$), that is, more than a thousand times.

Tables 2-4 show the increase in *Azotobacter* and *Rhizobium* bacteria amounts (wort agar medium) as well as in total microbiota (solid Zvyagintsev's medium).

The data in tables 1-4 testify to the sharp increase in microorganisms amounts within 50°-60° C. temperature range, while temperature increase over 60° C. causes bacteria inhibition, their transition to suspended animation state and spore formation followed by their regeneration under favorable conditions.

At the same time the concentration of viable bacteria decreases by one or two digits on average but less than $10^7$ CFU.

Temperatures higher than 80° C. bring about the destruction of most microbiota and its amount reduction.

Example 2

To increase the fertility of sandy loamy soils and their water-retaining properties, use is made of the following mixture: 200 kg of valley peat and 40 kg of the Californian worm biohumus. Peat humidity is 60%, it contains 20% ash, 80% organic matter, carbon content mainly in the form of humic substances being about 30% relative to the dry organic matter amount. The total nitrogen amount in the peat is about 2.8%. The total microorganism content of the mixture is $2.2 \cdot 10^4$ CFU/ml, organic carbon—25.6%, nitrogen—1.6% per 100 g dry mixture. Raw materials are carefully sifted to remove mechanical impurities in the form of pebbles and wood residues, loaded into a separate tank filled previously with 400 l water and mixed thoroughly by circulating them with a pump. As a result, a "coarse" aqueous suspension fertile soil-water is obtained. The suspension is pumped to the device in the form of a closed circuit consisting of a 670 liter vertical tank with a piping system connected to an electric pump with a capacity of 90 m$^3$/h and an outlet pressure of 4 Bar and a 90 kW electric drive. Between the pump and the tank a turbulator is installed in the form of a hydrodynamic nozzle with a relative contraction close to two and a smoothly streamlined obstacle in the form of a ball with a flow blocking factor close to 65%. The spherical form of obstacles is traditionally used to create developed turbulent currents reaching the critical Reynolds numbers which characterize turbulence degree.

To control the nozzle operation in the turbulent mode with no cavitation ruptures, manometers $P_1$ and $P_2$ are installed to measure pressure before and after the nozzle correspondingly. In the case of cavitation ruptures, the difference in the manometer readings changes discontinuously towards the reading increase.

After loading a portion of suspension to be processed, a pump is switched on and the liquid medium circulates through a closed circuit: tank—pump—turbulent nozzle—tank. As a result of particles turbulent friction in the nozzle, on the tank and pipeline walls as well as shear stresses in the liquid, the suspension is heated. The manometer readings are $P_1 \approx 7.43$ Bar, $P_2 \approx 7.33$ Bar, the difference being $\Delta P = 0.1$ Bar, which meets the condition $0.1$ Bar $\leq \Delta P \leq 0.2$ Bar controlling the absence of cavitation currents.

Due to the fact that the specific energy intensity of the process is close to $W = 0.134$ kW/kg, which corresponds to the condition (2) specified in claim 8, the heating rate of the processed suspension is 1.8 deg/min, which does not exceed the value of 2 deg/min.

In the process of cyclic processing, the suspension to be processed is sufficiently slowly heated, which facilitates the transition of the raw material useful components into a water-soluble form. The use of these useful components which have passed into an accessible form by bacteria leads to their intensive growth.

TABLE 5

General and water-soluble forms of nitrogen and carbon (on a dry matter basis)

| Process temperature (° C.) | Total nitrogen N, mg/100 g | Water-soluble nitrogen (filtrate mg/kg) | | | | Total carbon, g/100 g | Water-soluble carbon, g/100 g | Relative fraction of soluble carbon to total carbon, % |
|---|---|---|---|---|---|---|---|---|
| | | Nitrate $NO_3$ | Ammonium $NH_4$ | Nitrite $NO_2$ | Total nitrogen N | | | |
| Control (raw stuff) 20° C. | 1633 | 94.7 | 35.1 | 0.55 | 130.35 | 25.86 | 0.173 | 0.67 |
| 46° C. | 1591 | 122.0 | 50.3 | 0.74 | 173.04 | 27.24 | 0.571 | 2.13 |
| 52° C. | 1562 | 85.3 | 25.3 | 1.4 | 112.0 | 26.83 | 0.734 | 2.74 |
| 60° C. | 1640 | 79.0 | 30.3 | 2.2 | 111.5 | 26.72 | 1.241 | 4.62 |
| 70° C. | 1587 | 69.7 | 52.0 | 2.2 | 123.9 | 27.24 | 1.730 | 6.40 |
| 80° C. | 163.1 | 58.0 | 45.8 | 2.2 | 106.0 | 25.86 | 1.927 | 7.51 |

Table 5 shows the increase in the water-soluble fraction of carbohydrates and nitrogen as the processing temperature increases.

Water-soluble nitrogen was measured in 3 forms: nitrate $NO_2$, nitrite $NO_3$ and ammonium $NH_4$. It can be seen from Table 5 that within a short time when the temperature reaches about 46° C. from the initial 20° C., the total amount of water-soluble nitrogen 173 mg/kg has grown by approximately 35% relative to the water-soluble nitrogen of the raw material 130.3 mg/kg taken at 20° C. All analyzes hereafter (unless otherwise specified) are given relative to dry matter.

Particularly noteworthy is the active growth of ammonium nitrogen, the main construction material for bacterial membranes. The amount of $NH_4$ nitrogen increases by more than 50% when the temperature reaches about 46° C. As a result, in the temperature range from 40° C. to 50° C. bacteria begin to proliferate actively, hundreds of times faster than under natural conditions. Thus, at the temperature of about 52° C. the amount of ammonium nitrogen drops significantly, lower than its amount in the feedstock because nitrogen is not used for forming bacterial membranes. Consequently the construction material of deformed membranes becomes available for determining chemically the water-soluble nitrogen amount, which explains its rise from the value of 25.3 mg at 52° C. to 52.0 mg at 70° C. Such behavior of ammonium nitrogen is typical of the method described.

Insoluble carbon humic compounds in the feedstock (starting humus-containing soil) turn into soluble ones, mainly humic and fulvic acids. That is why the organic fertilizer obtained after water dilution has an opaque dark color.

Active mixing, slowly growing comfortable temperature of the nutrient medium, easily digested food with available forms of complex sugars in the form of water-soluble carbohydrates and minerals intensify the process to the maximum possible values. A "soft" turbulent effect on the processed medium prevents the selective growth of small and death of relatively large bacteria forms which is characteristic of the well-known methods that use the hard mechanic effect, for example, cavitation, for the purpose. The above features that characterize the invention allow maximum maintenance of the bacterial profile or "portrait" of the feedstock aboriginal microorganisms.

The results of bacterial concentration growth are shown in Table 6 which shows that, as the temperature reaches 60° C., the intensive growth of microflora ceases, limited to a value of $3.0 \times 10^8$, which can be considered the end of the first stage of processing.

TABLE 6

Total bacterial microbiota amount in the studied liquid soil samples (1: $10^{-4}$ titer, Zvyagintsev medium)

| $N_o$ | Temperature | Average number of colonies | Notes |
|---|---|---|---|
| 1. | 20° C. (feedstock) | $2.2 \cdot 10^4$ | up to 7 colonial morphotypes |
| 2. | 30° C. | $3.5 \cdot 10^6$ | up to 7 colonial morphotypes |
| 3. | 50° C. | $2.5 \cdot 10^8$ | up to 7 colonial morphotypes |
| 4. | 60° C. | up to $3.0 \cdot 10^8$ | The widest quality spectrum of morphotypes |
| 5. | 70° C. | $6.0 \cdot 10^7$ | colonial types of Pseudomonas and others in suspended animation state |
| 6. | 80° C. | up to $4.0 \cdot 10^6$ | bacillary forms in spore forms and suspended animation |

After the temperature of 60° C., the second stage of the bacteria hardening begins accompanied by their simultaneous transfer to spore forms and/or the state of anabiosis. At the same time microorganisms concentration decreases vastly (from $3 \cdot 10^8$ at 60° C. to $4 \cdot 10^7$ at 80° C.) because of some bacteria destruction and some bacteria transition to the state of anabiosis and spore forms.

At this stage it is especially important to avoid dead zones inside the tank, that is, zones with insufficiently crushed solid soil particles and lower temperatures insufficient for the transition of microorganisms into spore forms and the state of anabiosis. Accordingly, this can lead to a drastic reduction in the fertilizer shelf life, pack swell, bloat and the like.

Therefore, the equality of temperatures $T_1 = T_2 \ldots T_n$ on the tank outer surface ensures the control of the uniform heating of the entire suspension volume processed in the tank. The equality of temperatures on the surface and inside the entire volume is due to the high degree of heat and mass transfer coefficient as a result of active pumping and turbulent mixing of the entire processed liquid.

It is especially important to note the equality of the temperature values top-down, in particular, in the upper and lower parts of the tank where the probability of dead zones occurrence is the highest. This is due to the fact that the viscosity of the processed suspension increases as the temperature rises and after reaching the temperature of 50° C. it can increase tenfold. This is due to carbon transfer into a form that is accessible to bacteria, i.e. water-soluble form, and primarily into lignin and humic compounds, as well as cellulose transition into dextrins, protopectin—into pectin and so on, which leads to a significant increase in the liquid medium rheological properties.

The temperature increase in the second stage is targeted to 80° C. Its further increase, as experiments have shown, leads to irreversible processes of some microorganism spore forms death and to "welding" high-molecular polysaccharides of lignin type. In this case the final product becomes poorly soluble and substandard because of the bacterial content which is below $10^7$ CFU/ml. Naturally the bacterial profile of such a fertilizer differs significantly from the initial profile of natural raw materials, shifting towards thermophilic bacteria.

Note that usually the transition of bacteria into spore forms begins at temperatures around 60° C., at a temperature above 70° C. it becomes active and at 75°-80° C. its activity practically ends.

To increase the number of microorganisms at the end of the first stage, it is advisable in certain cases to make a temporary pause as one else processing stage, thereby fixing the optimal temperature of bacteria proliferation. To do this, it is enough to switch off the pump for a while.

In any case, the expedience of a pause is determined in each case experimentally, on the basis of microbiological tests analysis.

Example 3

The same as in example 2. The power of the pump drive is increased to 150 kW. Power dimensional factor $\overline{N}=0.22$ kW/kg exceeds the upper permissible limit equaling 0.2 kW/kg of the inequality (2), p. 8.

Substandard final product is obtained because of high heating rate (more than 2 deg/min). The total amount of bacteria does not exceed $10^5$ CFU/ml, which testifies to microorganisms inability to adapt to too fast medium heating.

Example 4

The same as in example 2. The power of the pump drive is decreased to 30 kW. Substandard final product is obtained because of dispersion particles heterogeneity. Dimensional factor $\overline{N}=0.045$ exceeds the lower permissible power limit $\overline{N}=0.1$ kW. Some suspension particles are more than 50 micron size which can cause a sprayer filter or a drip hose injector clogging. The flow energy is not enough for crushing effectively the medium under processing. In this example, in the process of heating the temperature at different points of the tank surface was different. Therefore, when the temperature reaches 80° C. in the upper part of the tank, in its lower part the temperature reaches only 68° C., which testifies to the presence of dead zones due to the insufficient provision of power.

Example 5

The same as in example 2. Pressure at the pump outlet is increased to $P_1$=12 Bar. As a result, the pressure difference on the turbulent nozzle increases to $\Delta P=P_1-P_2=0.27$ Bar. The device switches to cavitation mode because of the violation of the condition (1) specified in p. 8 of the claims according to which the maximum pressure difference on the nozzle should not exceed $\Delta P$=0.2 Bar. High-frequency noise appears at frequencies close to ($17.5\cdot10^3$ Hz), which accompanies the destruction of cavitation bubbles. In the product obtained the percentage of relatively "large" nitrogen-fixing bacteria of the *Rhizobium* type (tubercular bacteria) has been reduced three times compared to the natural profile (see Table 6). This testifies to the fact that the microorganisms that are important for plants and soils and that accumulate nitrogen from the atmosphere in tubercles have been destructed. The final product is substandard as the bacterial profile has higher content of small bacteria (1-2 micron size or even smaller), thus it fails to provide plants with necessary nutrients.

Example 6

The same as in example 2. Pressure $P_1$ at the pump outlet is decreased to 5 Bar. As a result the pressure difference at the nozzle $\Delta P$ decreases to 0.08 Bar which violates the condition (1) specified in p. 8 of the claims going beyond the lower limit $\Delta P$=0.1 Bar.

Substandard product is obtained as the fertilizer particle size exceeds 50 micron which causes sprayer filter clogging.

Hydrodynamic effect on the processed medium is insufficient. The resulting product has a liquid consistency which is explained by the fact that lignin contained in peat has not been converted to water-soluble form. Accordingly, natural humic compounds remain unavailable to soil microorganisms. The ultimate concentration of microorganisms is low ($10^5$-$10^6$ CFU/ml), which is not enough for effective presowing seeds treatment (inoculations).

Example 7

Fertilizer is supposed to be used for growing soybeans on light grey desert soils containing not more than 1.5% humus. Use has been made of the same device as in example 2. 200 kg of light grey desert soil with the initial natural microflora content of $2.7\cdot10^4$ CFU/ml and 0.52% nitrogen and 8% carbon content (on the dry matter basis) has been used.

At the end of the first stage of the cyclic processing the content of water-soluble carbon increases to 370 mg and water-soluble nitrogen—to 25 mg/100 g product. It is below the lower limit (40 mg) for the standard product in compliance with the preferred embodiment as claimed in claim 10. Accordingly, because of the nutrients low concentration in grey desert soil, the soil microorganism concentration increases only to $1.2\cdot10^6$, thus using the proposed technology is inexpedient because the final microorganism concentration in the final product according to the invention should be at least $10^7$ CFU/ml.

At the same time increasing the amount of grey desert soil in the loaded portion to 240 kg with the aim of ensuring more beneficial properties of the final product leads to higher viscosity of the suspension which makes impossible an active circulation because of dead zones emergence.

This leads to the conclusion that just grey desert soil cannot be a proper feedstock for a quality biofertilizer, it requires additions of biohumus, sapropel, manure, etc which contain more microorganisms and organic substances.

Example 8

The same as in example 7. 200 kg grey desert soil are supplied with 20 kg biohumus on the basis of cow manure, 32% moisture with an initial carbon content of 25.3% and total nitrogen of 2.63% based on dry matter. The initial concentration of biohumus bacteria is $3.2\cdot10^8$ CFU/ml.

On processing the final quality product demonstrates fungicide properties because natural bacteria have been substituted for pathogenic fungi.

High nutritional properties of the product obtained as an organic fertilizer are due to a significant amount of soluble carbon (980 mg) and soluble nitrogen (65 mg) per 100 g of product, as well as to high content of trace elements.

As a result of applying the obtained product to clay soils of southern Ukraine, the yield of soybeans under irrigation increases by 12% on using 1l fertilizer per 1000 kg seeds (inoculation) and by 18.2% on a single spraying, the dose being 2 l/ha per 200 l water at the stage of 4-6 true leaves.

Soya plants remain practically sound. The activity of the soil microflora which is determined by carbon dioxide release from soil has increased almost 2.5 times. It is important to note that in July the soil temperature rises to 60° C., however, the natural bacteria hardened at the second processing stage have survived and actively reproduced at extreme temperatures of southern Ukraine.

As numerous experiments have shown, traditional biological products based on nitrogen-fixing bacteria (so-called "inoculants") grown on artificial media practically lose their effectiveness in such extreme conditions.

Example 9

When cultivating melons on poor sandy soils it is advisable to use mixtures poor in organic matter, colonized by oligotrophic bacteria characteristic of sandy soils. To produce fertilizers the following mixture of soils is used: 40% sandy soils, 30% peat, 20% sapropel, 10% biohumus. The mixture contains about 19.7% of total carbon and 2.3% of nitrogen based on dry matter.

Microorganism concentration in this soil mixture is $1.2 \cdot 10^5$ CFU/ml. The feedstock contains relatively great amount of oligotrophic bacteria typical of sandy soil and valley peat. These bacteria can develop at low nitrogen concentration in well-aerated sandy soil.

On using the described technology and the processing mode described in Example 2, a quality product is produced, its bacteria content being $1.7 \cdot 10^9$, water-soluble carbon making 690 mg and nitrogen making 78 mg per 100 g of dry matter with highly homogenous structure. The sand particles are filtered before packing. The product contains a large number of biologically active substances inherent in sapropel and organic biohumus.

The final product has been used on sandy testing grounds for cultivating organic melons and watermelons. The results of cultivating organic non-irrigated watermelons are given in table 7. The fertilizer made according to the invention is called "Product".

TABLE 7

Cultivation of organic watermelons

| № | Experiment variant | Yield, t/ha | ± to control 1 t/ha | ± to control 1 % | ± to control 2 t/ha | ± to control 2 % |
|---|---|---|---|---|---|---|
| 1 | Control 1 | 17.2 | — | — | −0.6 | −3.5 |
| 2 | Control 2 (treating seeds with water) | 17.8 | +0.6 | +3.5 | — | — |
| 3 | Treating seeds with "Product" (1 l/t) | 18.9 | +1.7 | +9.9 | +1.1 | +6.2 |
| 4 | Treating seeds with "Product" (2 l/t) | 19.4 | +2.2 | +12.8 | +1.6 | +9 |
| 5 | Spraying plants with "Product" (2 l/ha) | 20.2 | +3 | +17.4 | +2.4 | +13.5 |
| 6 | Spraying plants with "Product" (4 l/ha) | 20.6 | +3.4 | +19.8 | +2.8 | +15.7 |
| 7 | Treating seeds with "Product" (1 l/t) + spraying plants with "Product" (2 l/ha) | 21.2 | +4 | +23.2 | +3.4 | +19.1 |
| 8 | Treating seeds with "Product" (1 l/t) + spraying plants with "Product" (4 l/ha) | 22.1 | +4.9 | +28.5 | +4.3 | +24.1 |
| 9 | Treating seeds with "Product" (2 l/t) + spraying plants with "Product" (2 l/ha) | 22.6 | +5.4 | +31.4 | +4.8 | +27 |
| 10 | Treating seeds with "Product" (2 l/t) + spraying plants with "Product" (4 l/ha) | 22.8 | +5.6 | +32.5 | +5 | +28.1 |

HIP 05 t = 0.51

The main concise conclusions of using the product are presented below:
- seedling emergence 2 days and fruits ripening 8 days earlier than in control;
- 2-2.5 times increase in soil organisms biological activity which testifies to the increased activity of soil processes and nutrition improvement;
- 20-22% reduction of water consumption coefficient, i.e. the amount of groundwater needed to form 1000 kg fruit;
- 9.9% increase in yield with pre-sowing seed treatment and 32.5% increase with the product combined application.

Example 10

Biofertilizer is used for growing apple-trees on clay soil. Valley peat with Ph=6.8 acidity is applied. Initial microorganism concentration in the feedstock is $1.5 \cdot 10^4$ CFU/ml. The amount of lignin in peat is 3.6% based on dry matter.

As a result of the proposed method use and the final heating up to 80° C. at the second stage, a homogenous gel-like product has been obtained. The ultimate total concentration of microorganisms that have entered the state of suspended animation and spore forms, is about $2.2 \times 10^8$ CFU/ml. After packaging, the product is cooled to −2° C. This is done for the purpose of hardening microorganisms.

Apart from organic fertilizer properties, the product has the properties of a natural adaptogen which is capable to restore plants promptly after chemical treatment, adverse weather conditions including crops freezing during winter. First of all it is due to the carbon conversion into water-soluble forms as humic acids. As the study has shown, the content of water-soluble humates (see Table 5) increases tenfold reaching 0.1-1% of the fertilizer dry weight. The product triple application by spraying, the dose being 6 l/ha, made it possible to restore the apple orchard productivity after late frosts in 2017.

The fertilizer gel-like form reduces fertilizer consumption by 30-40% due to its better adhesion to leaf surface.

Example 11

The same as in example 9. The production process is restricted to the first stage and stopped at 55° C. medium temperature which is immediately followed by packing. Live bacteria concentration is higher than $10^{11}$. The bacteria have not entered the state of suspended animation or spore forms, thus the product is substandard. Active reproduction of soil microflora caused packages bloating and depressurizing, thus making the biofertilizer transportation impossible.

Example 12

In order to compare the final products made by using cavitation and turbulence phenomena, the same sequence of operations and the device described in example 2 are used, the mixture content being the same as well. The turbulent nozzle of this example is replaced with a direct-flow cavitational mixer with a cavitator in the form of a truncated cone that clogs the flow by 85% with regard to the area of the nozzle minimum cross-section.

The pressure at the $P_1$ pump outlet has been increased to 11.2 Bar. Thus the pressure difference $\Delta P$ at the nozzle increased to 0.35 Bar which indicates that the nozzle has changed over to the cavitation flow mode. The emergence of cavitation is accompanied by specific cavitation noise. All other parameters of the process are identical. To get the bacterial profile before and after applying the invention the following microorganisms tested on the conventional nutrient medium have been used:
1. Nitrogen-fixing bacteria which include *Rhizobium*, Ashby nutrient medium;
2. Bacteria capable of absorbing organic forms of nitrogen in soil, SAA (starch-ammonia agar) nutrient medium;
3. Oligotrophic bacteria which grow well on depleted soils, SA (starvation agar) nutrient medium;
4. Phosphorous-mobilizing bacteria of the *Bacillus subtilis* type Gause's nutrient medium;
5. Fungi microflora including micromycetes, Czapek's nutrient medium;
6. The total amount of microorganisms, Zvyagintsev's nutrient medium.

Table 8 shows comparative round results of the bacteria concentrations in the feedstock diluted with water and mixed to a suspension of 80% humidity before and after processing by means of cavitation and turbulence phenomena.

TABLE 8

| № | Medium | Initial suspension peat-water | $r_1$ (%) | A Turbulence (CRU/ml) | $r_2$ (%) | B Cavitation (CFU/ml) | $r_3$ (%) |
|---|---|---|---|---|---|---|---|
| 1 | Ashby | $3.0 \cdot 10^5$ | 10 | $1.1 \cdot 10^8$ | 12 | $0.2 \cdot 10^7$ | 3 |
| 2 | SAA | $6.1 \cdot 10^5$ | 20 | $2.2 \cdot 10^8$ | 24 | $0.9 \cdot 10^7$ | 12 |
| 3 | SA | $7.6 \cdot 10^5$ | 25 | $1.8 \cdot 10^8$ | 21 | $1.2 \cdot 10^7$ | 17 |
| 4 | Gause's | $1.1 \cdot 10^6$ | 35 | $2.8 \cdot 10^8$ | 32 | $4.1 \cdot 10^7$ | 56 |
| 5 | Czapek's | $3.2 \cdot 10^4$ | 1.0 | $6.9 \cdot 10^6$ | 0.8 | $1.5 \cdot 10^6$ | 2.1 |
| 6 | Zvyagintsev's | $3.1 \cdot 10^6$ | 100 | $8.7 \cdot 10^8$ | 100 | $7.3 \cdot 10^7$ | 100 |

The values of $r_1$, $r_2$, $r_3$ (%) show the percentage of bacterial components in the total amount of microorganisms bred in Zvyagintsev's medium and taken for 100% (table 8).

After processing by turbulence (A) and cavitation (B) this amount changes but under turbulence the amount of relatively "large" bacteria bred on Ashby medium (nitrogen-fixing)—12% and on SA medium (oligotrophic)—21% remains practically the same compared to their amount in the initial suspension (10% and 25%, respectively). But under cavitation the share of these bacteria drops sharply to 3% and 17%, respectively.

At the same time the share of relatively "small" phosphorous-mobilizing bacteria (Gause's medium) practically does not change (35% in the initial soil suspension and 32% after turbulence process). It should be noted that after cavitation it increases sharply by more than 1.6 times and reaches 56%.

But the percentage of fungi in micromycetes practically does not change from 1% in the initial feedstock up to 0.8% under the influence of turbulence and changes greatly influenced by cavitation, doubling to 2.1% of the total microbiota amount.

This testifies to the fact that the proposed method of "gentle" soil suspension processing by turbulence preserves the natural profile ("portrait") of fertile soils while "hard" processing by cavitation deforms it considerably destroying relatively large bacteria (3-10 microns) and cultivating small ones (1-2 microns).

The emergence of cavitation is accompanied by a typical cavitational noise, the other process parameters being the same.

At the same time the patented method using the "soft" processing mode based on turbulence increases the availability of fertile soil beneficial components by increasing the efficiency of the final product use also as a mineral organic biological fertilizer.

Various aspects of the invention to be patented are most effective for the restoration of soil fertility depleted by fertilizers and pesticides overuse, under flooding, etc.

Example 13

In order to increase yields and restore soil fertility the biological fertilizer according to the invention has been used in growing the Aratta soybean variety under irrigation.

Microbiota in the soil for the crop is almost absent and amounts to $10^2$-$10^3$ CFU/ml. The humus amount in the soil is not higher than 1.2%, which is not enough for soybean cultivation.

To increase soybean productivity, fertile organic soil of the black earth profile has been used after growing on it the same soybean variety in the previous year.

The amount of nitrogen-fixing *Rhizobium* bacteria in the soil is $8 \cdot 10^7$. The total microbiota amount is not less than $10^8$-$10^9$, that of carbon—12%, nitrogen—more than 2.5% on a dry matter basis. Thus the potential fertility of the soil is very high.

On processing according to the proposed technology, a quality product has been obtained, nitrogen-fixing bacteria prevailing in its profile ($2 \cdot 10^8$), water-soluble nitrogen and carbon making 120 mg and 570 mg, respectively, on a dry matter basis.

The results of studying the obtained biological fertilizer are given in table 9.

TABLE 9

Indicators of nitrogen-fixing capacity and the *Aratta* soybean variety productivity

| № | Variants | Tubercle weight per plant, g | Tubercle weight per ha, kg | Yield, center/ha | Increase, % |
|---|---|---|---|---|---|
| 1 | Treatment with water (control) | 0.10 | 66.0 | 18.1 | 0 |
| 2 | Seed treatment with Product (1 l/t) | 0.26 | 171.6 | 19.8 | 9.4 |
| 3 | Spraying 1% Product solution on vegetating plants (2 real leaves) | 0.45 | 317.0 | 20.5 | 13.3 |

TABLE 9-continued

Indicators of nitrogen-fixing capacity and the *Aratta* soybean variety productivity

| No | Variants | Tubercle weight per plant, g | Tubercle weight per ha, kg | Yield, center/ha | Increase, % |
|---|---|---|---|---|---|
| 4 | Seed treatment with Product (1 l/t) + spraying 1% Product solution on vegetating plants (2 real leaves) | 0.65 | 432.0 | 20.7 | 14.4 |

Consequently, the studies conducted have found out that the application of the proposed biological fertilizer affects significantly the productivity, the formation of tubers and their weight.

Thus, seed treatment with Product (1 l/t)+spraying 1% Product solution on vegetating plants (2 real leaves) cause tubers weight increase to 0.55 g per plant compared to the control, while the total tubers weight increased by 366.0 kg/ha.

The yield increase varies from 9.4% to 14.4%, which in terms of economic indicators gives an estimated 10-15 UAH additional income per each UAH invested in organic fertilizers.

INDUSTRIAL APPLICABILITY

The studies conducted have shown that based on the state of soil, plant species and variety, cultivation technology, etc the proposed invention makes it possible to select the feedstock component composition by optimizing its application method to ensure a commercially significant industrial application. The proposed technology is particularly relevant in present day conditions when soils are depleted by irrational crop rotation, chemical pollution, natural disasters such as droughts and late frosts, global warming on the planet.

The naturalness and organicity of the proposed technical decisions on obtaining liquid organic biological fertilizer and its subsequent application is that by transferring a small amount of fertile soil from one place to another it is possible to restore fertility and increase yields on large areas in a short period of time at a minimal labor and material cost.

It is also important to note that the application of the biological fertilizer of a certain microbiotic portrait produced according to the invention also leads to the reduction in herbicide and fungicide use up to 30% of the recommended doses.

The invention claimed is:

1. A method of obtaining a liquid organic biofertilizer for soils or plants that is colonized by natural soil microorganisms, the method comprising:
   a) preparing, sorting and crushing a portion of a starting humus-containing soil or soil mixture, the starting humus-containing soil or soil mixture having an organic carbon in an amount greater than 10% and an organic nitrogen in an amount greater than 1% and having colonies of natural soil microorganisms, the colonies of natural soil microorganism having a concentration in the starting humus-containing soil or soil mixture being equal to or greater than $10^4$ CFU/ml;
   b) mixing the crushed portion of the soil or soil mixture with water to produce a water suspension;
   c) creating a running flow of the water suspension within a closed circuit with restricted access to oxygen; d) cyclic processing of the running flow of the water suspension within the closed circuit with restricted access to oxygen by using a turbulence effect so as to preclude cavitation and to provide crushing solids in a processed medium of the running flow of the water suspension, and uniform heating of an entire volume the processed medium with a temperature growth rate not exceeding 2° C./min; the cyclic processing comprising at least a first stage and a second stage, wherein:
   the first stage includes providing an initial heating of the processed medium, extracting of carbon- and nitrogen-containing substances from the processed medium, transiting the substances into water-soluble forms with simultaneous crushing solids in the processed medium and obtaining a homogeneous processed medium with carbon- and nitrogen-containing substances in water-soluble forms causing a growth of colonies of natural soil microorganisms being present in the homogeneous processed medium, and by reaching a predetermined final temperature upon the initial heating the growth of colonies of the natural soil microorganisms present in the starting humus-containing soil is achieved with a concentration exceeding $10^8$ CFU/ml and a uniform colonization of the homogeneous processed medium with carbon- and nitrogen-containing substances in water-soluble forms by these microorganisms is achieved;
   second stage includes providing a further heating of the homogeneous processed medium and a further crushing solids in the homogeneous processed medium to result in a hardening of the natural soil microorganisms present in the homogeneous processed medium, transiting the microorganisms into a state of anabiosis and spore form, and crushing solids in the homogeneous processed medium to a size ranging between 10 and 50 microns; and
   e) removing the homogenous processed medium from the closed circuit after finishing the second stage followed by a cooling of the medium to obtain a liquid organic biofertilizer, the liquid organic biofertilizer containing carbon- and nitrogen-containing substances in water-soluble forms, solids with a size of 10-50 microns and the hardened natural soil microorganisms present in the state of anabiosis or spore form and in the concentration exceeding $10^7$ CFU/ml.

2. The method of claim 1, wherein the final temperature of the initial heating of the homogeneous processed medium at the first stage of the cyclic processing is about 50° C.

3. The method of claim 1, wherein a final temperature of the further heating of the homogeneous processed medium at the second stage of the cyclic processing is in a range of about 50°-80° C.

4. The method of claim 1, wherein the cooling is carried out within a temperature range from +40° C. to −4° C.

5. The method of claim 1, wherein the starting humus-containing soil is selected from the group consisting of peat, forest soil, sapropel, bottom sediments of freshwater estuaries and lakes, algae, biohumus, black earth, grey desert soil and leonardite.

6. The method of claim 1, wherein the liquid organic biofertilizer is obtained in a gel form when a lignin content in the starting humus-containing soil or soil mixture exceeds 2% based on a dry weight.

7. The method of claim 1, wherein the liquid organic biofertilizer is obtained with humus water-soluble acids content exceeding 0,1% when a humus content in the staring humus-containing soil or soil mixture exceeds 3%.

8. The method of claim 1, wherein the natural soil microorganisms that transit under the hardening into the state of anabiosis or spore form are the microorganisms selected from the group consisting of nitrogen-fixing bacteria, bacteria that assimilate organic soil nitrogen, phosphorous-mobilizing bacteria, oligotrophic bacteria that grow on depleted soils, and fungal microflora including micromycetes.

9. The method of claim 1, wherein the cyclic processing is carried out in the closed circuit with restricted access to oxygen by a vertical cylindrical tank, an electric pump connected to a lower part of the cylindrical tank and a turbulence device having a turbulence nozzle mounted after the pump and tangentially connected to an upper part of the cylindrical tank, the mode of turbulence effect on the medium processed in the closed circuit being provided so as to exclude cavitation and emergence of dead zones and to keep the following three conditions:

$$0.1 \text{Bar} \leq \Delta P \leq 0.2 \text{ Bar} \tag{1}$$

$$0.1 \frac{\text{kW}}{\text{kg}} \leq \overline{N} \leq 0.2 \frac{\text{kW}}{\text{kg}} \tag{2}$$

$$T1=T2 \ldots Tn \tag{3}$$

where ΔP=(P1−P2)—pressure difference before and after the turbulence nozzle (Bar), $$\overline{N} = \frac{N}{M} - \text{process specific energy consumption, kW/kg,}$$

N—pump electric drive power, kW,
M—processed fluid medium weight, kg,
T1=T2 . . . Tn—current heating temperature at measuring points distributed on an outer surface of the cylindrical tank which serve to control the uniformity of heating the entire volume of the medium processed in the closed circuit.

10. A liquid organic biofertilizer for soils or plants the biofertilizer comprising:
a water-soluble nitrogen and a water-soluble carbon;
solids with a size 10 and 50 microns; and
hardened natural soil microorganisms present in an anabiotic state or in a spore form and are uniformly populated in a concentration exceeding $10^7$ CFU/ml;
wherein the hardened soil microorganisms were obtained via a two-stage heating process of a medium prepared from a starting humus-containing soil or soil mixture, the starting humus-containing soil or soil mixture having an organic carbon in an amount greater than 10%, an organic nitrogen in an amount greater than 1%, and colonies of natural soil microorganisms with a concentration equal to or greater than $10^4$ CFU/ml.

11. The biofertilizer according to claim 10, wherein a content of the water-soluble nitrogen is at least 40 mg and a content of the water-soluble carbon is not less than 470 mg per 100 g of the biofertilizer on basis of a dry weight.

12. A method of treating soil, seeds or plants with using a liquid organic biofertilizer, the method comprising;
preparing the liquid organic biofertilizer;
adding a liquid or a crushed dry natural soil to the liquid organic biofertilizer to reduce a concentration of hardened natural soil microorganisms present in the biofertilizer to a concentration exceeding 104 CFU/ml, and
applying the reduced concentration biofertilizer to a soil before sowing or during a sowing period or treating seeds or plants with the reduced concentration biofertilizer during a vegetation period before harvesting;
wherein the liquid organic biofertilizer is prepared by:
crushing a portion of a starting humus-containing soil or soil mixture, the starting humus-containing soil or soil mixture having an organic carbon in an amount greater than 10% and an organic nitrogen in an amount greater than 1% and having colonies of natural soil microorganisms, the colonies of natural soil microorganism having a concentration equal to or greater than $10^4$ CFU/ml;
mixing the crushed portion of the soil or soil mixture with water to produce a water suspension;
creating a running flow of the water suspension within a closed circuit with restricted access to oxygen;
cyclic processing of the running flow by using a turbulence effect so as to preclude cavitation and to provide crushing solids in a processed medium of the running flow of the water suspension, and uniform heating of an entire volume of the processed medium with a temperature growth rate not exceeding 2° C./min; the cyclic processing comprising at least two heating stages.

13. The method of claim 12, wherein to improve a yield of a plant, the liquid organic biofertilizer is obtained by using as the starting humus-containing soil a fertile soil taken from a field where the plant was previously grown.

14. The method of claim 12, whereinto increase a fertility of depleted soil the liquid organic biofertilizer is obtained by using as the starting humus-containing soil a soil of a similar type as the depleted soil to which the fertilizer is added.

15. The method of claim 12, wherein to restore sandy and sandy-loam soil the liquid organic biofertilizer is obtained by using as the starting humus-containing soil a soil colonized by oligotrophic bacteria.

\* \* \* \* \*